(12) United States Patent
Tesar

(10) Patent No.: US 9,918,619 B2
(45) Date of Patent: Mar. 20, 2018

(54) HIGHLY CORRECTED RELAY SYSTEM

(71) Applicant: NOVADAQ TECHNOLOGIES INC., Mississauga (CA)

(72) Inventor: John Tesar, Tucson, AZ (US)

(73) Assignee: NOVADAQ TECHNOLOGIES, INC., Mississauga ON (CA)

( * ) Notice: Subject to any disclaimer, the term of this patent is extended or adjusted under 35 U.S.C. 154(b) by 160 days.

(21) Appl. No.: 14/278,833

(22) Filed: May 15, 2014

(65) Prior Publication Data

US 2014/0343362 A1 Nov. 20, 2014

Related U.S. Application Data

(60) Provisional application No. 61/823,575, filed on May 15, 2013.

(51) Int. Cl.
- *A61B 1/00* (2006.01)
- *A61B 1/002* (2006.01)
- *G02B 23/24* (2006.01)

(52) U.S. Cl.
CPC .......... *A61B 1/002* (2013.01); *G02B 23/2446* (2013.01)

(58) Field of Classification Search
CPC .. A61B 1/002; G02B 23/2446; G02B 13/146; G02B 23/24; G02B 23/2407; G02B 9/60; G02B 9/64; G02B 13/0095
USPC ........ 359/362–435, 353, 350–351, 359–360, 359/355–357, 754, 763, 796–797
See application file for complete search history.

(56) References Cited

U.S. PATENT DOCUMENTS

| | | | |
|---|---|---|---|
| 3,257,902 A | 6/1966 | Hopkins | |
| 5,005,960 A | 4/1991 | Heimbeck | |
| 5,684,629 A | 11/1997 | Leiner | |
| 5,892,625 A * | 4/1999 | Heimer | G02B 23/2446 359/665 |
| 6,347,010 B1 * | 2/2002 | Chen | G02B 23/08 359/402 |
| 6,490,085 B1 | 12/2002 | Zobel | |
| 6,853,485 B2 * | 2/2005 | Hoogland | G02B 23/2423 359/434 |
| 7,724,430 B2 * | 5/2010 | Kasai | A61B 1/002 359/434 |
| 2008/0273247 A1 | 11/2008 | Kazakevich | |
| 2011/0249323 A1 * | 10/2011 | Tesar | G01J 3/36 359/356 |
| 2013/0194667 A1 | 8/2013 | Inoue | |

OTHER PUBLICATIONS

Tomkinson, T. H. et al., "Rigid endoscopic relay systems: a comparative study," Appl. Opt. 35, 1996, pp. 6674-6683.

* cited by examiner

Primary Examiner — Scott J Sugarman
Assistant Examiner — Kristina Deherrera
(74) Attorney, Agent, or Firm — Lee & Morse, P.C.

(57) ABSTRACT

A highly corrected relay system for medical endoscopes or the like is provided. The system includes a plurality of bonded lenses that are selected to provide color correction from the blue region of the spectrum through to the near infrared region of the spectrum. The system allows co-located visible and near infrared images to be resolved on a single detector.

6 Claims, 3 Drawing Sheets in pairs original Hopkins (KS)

old Henke Sass Wolf

Hopkins II (KS)

Olympus

Other Known Lens Assemblies

Highly Corrected Relay System

HIGHLY CORRECTED RELAY SYSTEM

BACKGROUND OF THE INVENTION

There is interest on the part of physicians to visualize tissue and body structures in other waveband regimes beyond that of visible bands, which are generally considered to be in or near the range from 400 nm to 700 nm. The near infrared regions (700 nm to 900 nm) where dyes such as Indocyanine green (ICG) fluoresce and are used as a marker, and where tissue has added transparency, are of particular interest. Additionally, the resolution requirements of endoscopes have increased with the introduction of High Definition (HD) detectors used in video imaging owing to smaller and more numerous pixels than earlier NTSC or PAL formats. Accordingly, optical improvements for endoscopes enabling extended waveband performance, higher sampling frequencies, and depth penetration in the near infrared in addition to the normal visible region would be advantageous.

In both diagnostic and therapeutic procedures where endoscopes are used it is advantageous to provide guiding imagery and fluorescent markers. These are used in surgical procedures to extend the physician's visualization of tissues and structures to regions beyond his native capabilities. Accordingly, good visualization in the visible bands plus longer wave length regions outside of human vision are a desirable outcome.

It is well known that detectors made of silicon respond very well in the infrared region, although this capability is normally not used in medical imaging systems as the human eye does not see where silicon responds best, i.e. above 700 nm. As a consequence, optical instruments for surgery have more than ignored this detector capability as it is outside of human vision, but purposefully block it because NIR detector response doesn't correspond to a primary color component of vision, i.e. red, green and blue. Normal imaging systems and the silicon response is binned by primary colors, either by color filters over individual pixels in the case of a single detector or larger color filters used to divide the entire beam path into red, green and blue paths for their own detectors. This later configuration is usually called a three-chip camera. A NIR detector response can be thought of as a black and white response. The challenge is to make this correspond to the optical path length of the visible regime.

Endoscopes are constructed to see deep within the body through a narrow opening or path and consist of numerous optical elements that can be grouped by functional requirements.

Rod lens assemblies or relay lenses are used in grouped pairs such as 3 pairs or 5 pairs and are required to re-image the product of the endoscope objective lens assembly to form an image at the field stop of the endoscope. An ocular or coupling lens for video use then views the combination of field stop and image. The longitudinal chromatic aberrations of existing endoscope relays, when used outside of visible wavebands, add significantly to a displacement of focal points, by wavelength, with longer wavelengths falling substantially behind that of the visible images focal points. This outside of visible waveband displacement error is cumulative, the sum of which is too large for the physician's expectation of, and need for, high resolution. This is particularly troublesome when attempting to resolve fine detail in vascular imaging, nerve imaging, and/or tumor margins in the near infrared spectrum with endoscopes designed for use in the visible spectrum.

Larger diameter endoscopes generally have faster f-numbers than smaller diameter endoscopes. More optical performance is required of larger diameter endoscopes due to physician expectations that larger endoscopes have high resolution and the nature of optical correction that requires more effort be applied to correcting faster systems as the optical train is enlarged. The diameter to length ratio of a 10 mm endoscope is larger than that of a 2.8 or 4 mm diameter endoscope, resulting in improved brightness and more resolution. 10 mm diameter endoscopes, and endoscopes of similar diameter, have relay systems that operate at approximately 1:6 (F 6) while 4 mm diameter endoscopes have relays that operate at approximately 1:7 (F 7), with smaller endoscopes operating at a correspondingly lower F-number.

U.S. Pat. No. 3,257,902 to Hopkins taught that filling the air spaces within an endoscope relay with glass rods substantially increased the operating F-number of an endoscope over that of existing endoscopes, which used cemented doublets widely spaced to produce a telecentric relay system. This resulted in brighter images and better diagnosis in visible wavebands.

It had been well known that a telecentric design was a requirement for producing a relay system without substantial vignetting. T. H. Tomkinson, J. L. Bentley, M. K. Crawford, C. J. Harkrider, D. T. Moore, and J. L. Rouke, "Rigid endoscopic relay systems: a comparative study," Appl. Opt. 35, 6674-6683 (1996).

To produce a non-vignetting telecentric relay at a fast F-number has been taught in U.S. Pat. No. 5,005,960 to Heimbeck and U.S. Pat. No. 5,684,629 to Leiner. These references show the production of well-corrected images in the center of the field in visible wavebands, though in most cases it is an achromatic correction due to the limited number of degrees of freedom. Residual aberrations such as astigmatism and coma are typically corrected for off axis field points in endoscopes by use of offsetting aberrations in the objective lens assembly. In particular, it is well known that field curvature is produced by positively curved elements, and in almost all cases the relay systems of endoscopes are composed of positively powered surfaces at their respective air-glass interfaces on each end of the rod assembly. There is a large amount of field curvature to be compensated for in the objective, which is successfully done for visible wavebands in present endoscopes.

When one adds the demand of high correction in a waveband outside of the visible (e.g., near infrared correction) it becomes necessary to add more degrees of freedom to the relays in the form of additional lens elements of differing materials. Endoscopic relays with 2 materials such as U.S. Pat. No. 5,005,960 provide fine achromatic correction on axis, but at 0.7 field and full field points there is significant uncorrected astigmatism, field curvature, coma and chromatic aberrations consistent with 2 element solutions, commonly called achromatic correction. Therefore 3 and 4 material solutions must be considered for super apochromatic performance, i.e., correction at 4 wavelengths, RGB in the visible and NIR (near infrared).

Additionally, market needs have changed with the introduction of high definition video. Where once manufacturers sought to lower parts count to reduce cost, which favored a limited number of elements, high definition video (HD) now requires higher performance so the number of elements must be rethought. By judicious use of radii and glass selection, additional glass elements can be added to the relay systems to take advantage of manufacturing efficiencies that are gained by the selection of longer radii because more of such lenses can be added to a fabricating tool by the opticians.

With short radii one, or a few, surfaces are produced on a grinding or polishing tool at a time. With longer radii a larger number can be produced in the same grinding or polishing time. Additionally, more lenses per tool yield more accurate results. Cemented components are more likely to be aligned properly than individual glass elements assembled in combination with metal spacers, so added elements should be considered as part of a bonded assembly.

Accordingly, there is a well-defined and long-felt need in the marketplace for an HD endoscope that can resolve both visible and near infrared light in approximately the same plane and, thus, can enhance visibility of tissues and structures for surgeons.

SUMMARY OF THE INVENTION

A highly corrected symmetric anastigmatic relay system for use in endoscopes is provided. The inventive system provides much wider waveband performance from blue light to NIR light than existing endoscopes, with the added advantage of sufficient numerical aperture to produce bright high contrast images.

A highly corrected relay assembly for endoscopes is constructed of a pair of rod lens assemblies symmetrical about a collimated area forming a limiting aperture; with a cemented doublet on a side of each plano plano rod element, the negative meniscus lens of the doublet adjacent to the stop consisting of a glass with an anomalous partial dispersion having a refractive index $n_e > 1.60$ and a dispersion or Abbe number of $v_e > 39$, the positive lens of this doublet having a glass having a refractive index $n_e < 1.54$ and a dispersion or Abbe number of $v_e > 60$, the cemented doublets furthest from the stop area each having a positive lens with an index $n_e > 1.75$ and a dispersion or Abbe number of $v_e > 37$, the negative lens of this doublet consisting of fused silica.

The inventive arrangement of the materials and radii of the doublets adjacent and bonded to the plano ends of the rod lens satisfy the condition of, from image forming side, a high index moderately dispersive element of positive power combined with a negative powered planoconcave element of fused silica, a plano plano rod element, a planoconvex positive powered element of very low index low dispersion material, and a meniscus negatively powered low index, but slightly higher index than it's near neighbor and also of low dispersion, but slightly more dispersive than it's near neighbor. The aforementioned lens assembly forms the first half of a symmetrical relay system about a stop. Following the stop is the same arrangement in reverse order.

The combination of a high index positive element of modest dispersion with the above combination of materials, in particular the fused silica negative member, and the other low index and low dispersion materials, forms a highly corrected wide waveband relay assembly that minimizes chromatic aberration over a wide range of wavelengths, and substantially corrects for spherical aberration, astigmatism, coma, and field curvature. There are a sufficient number of degrees of freedom within the specifications to minimize secondary spectrum and allow many pairs of relays to be used in conventional length endoscopes or bariatric length endoscopes, all the while correcting over a wide waveband range to allow co-located visible and near infrared images to be resolved on a single detector or, in the alternative, on multiplexed detector systems.

DETAILED DESCRIPTION OF THE PREFERRED EMBODIMENTS

Figure 1:
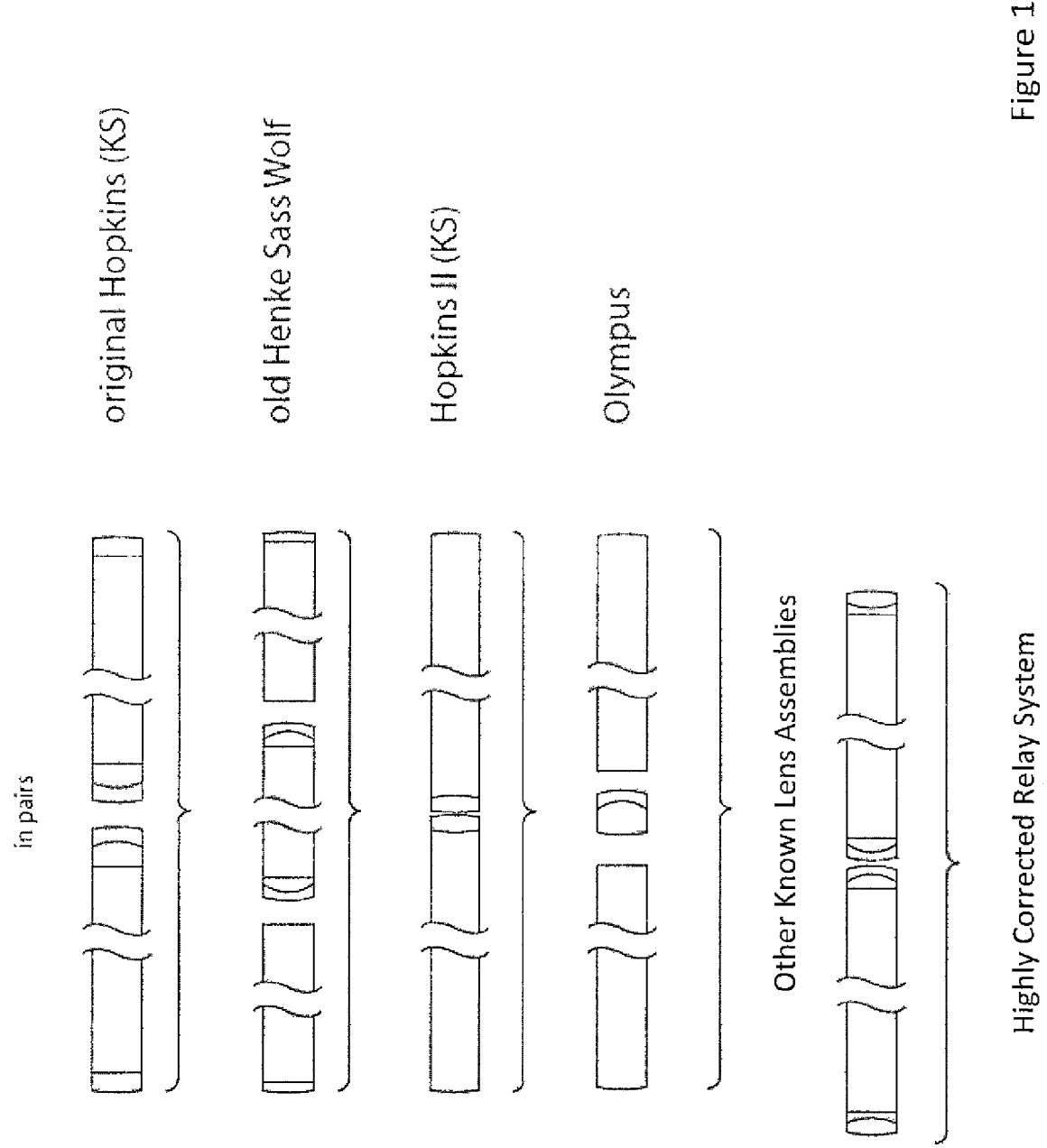
FIG. 1 is a comparison of an embodiment of the rod lens assembly of the present invention to other known lens assemblies.

According to one aspect of the invention, a rod lens assembly for endoscopy and the like is provided. The rod lens assembly comprises a plurality of bonded lenses selected to provide color correction from the blue region of the spectrum, corresponding to 400 nm at the lower limit, to the near infrared, corresponding to 900 nm at the upper limit, a minimum of Seidel aberrations left uncorrected, and correcting over a wide waveband range to allow co-located visible and near infrared images to be resolved on a single detector or, in the alternative, on multiplexed detector systems.

Another aspect of the invention provides a rod lens assembly for endoscopy containing one rod element per assembly in plano/plano form, and each assembly used in pairs of assemblies to re-image the product of the objective. The rod member is chosen to have a high index of refraction above $n=1.60$ of a flint material. Solely by way of example, F2HT glass can be used because of good blue light transmission. A crown glass such as N-PSK3 can also be used.

The design contemplates the use of pairs of assemblies centered around a stop between them with a positively powered low index element bonded on the stop side of the rod and a negatively powered very low index element bonded on the image side of the rod. The positively powered element has index of refraction below 1.48 and the negatively powered element on the opposite side of the rod has an index of refraction below 1.49, and a dispersion of >65. The positively powered element can be borosilicate glass and the negatively powered element can be fused silica.

According to one aspect of the invention, a rod lens assembly for endoscopes and the like comprising a doublet bonded to the rod surface on the stop side whose most adjacent lens to the rod is a positive powered element consists of a very low index glass with low dispersion. This positively powered element can be PK51, N-FK51 or N-FK51a, with borosilicate glasses such as BK7 or SK also being suitable.

According to yet another aspect of the invention, a rod lens assembly for endoscopes and the like, a 2-part combination forming a symmetrical pair of rod assemblies is provided. The rod assembly pair comprises, in order from either image side: a first bi-convex lens; a second plano-concave lens; a third elongated plano/plano rod lens; a forth plano-convex lens; a fifth meniscus lens; an air space containing a centered pupil and aperture stop position where upon the order of the next rod lens assembly is reversed.

According to one aspect of the invention, a rod lens assembly for endoscopes and the like with a telecentric image is produced. The 2-part combination of rod lens assemblies forms a telecentric image from a telecentric source. Between the two-rod assemblies is a collimated space with a centered limiting aperture.

According to yet another aspect of the invention, a rod lens assembly for endoscopes and the like, a 2-part combination forming a symmetrical pair of rod assemblies is provided. The assembly includes a plurality of lens elements and an aperture location, each element having a lens surface defined by a radius of curvature (r), a thickness (t), an index of refraction (n), and a dispersion value (v), the plurality of lens assemblies being spaced from each other, the object and the image by a distance (h). The rod lens assembly satisfies at least one or more of the following conditions:

1000<r4/r2 or r4=r2=approximately infinity;
−0.56<r3/r9<−0.81;
0.9<r8/r9<1.1 or r8=r9;
0.9<r10/r11<1.1 or r10=r11;
0.7<(h1+h2)/(h3+h4)<1.1;
0.95<h1+h2+h3+h4+T1+T2+T3+T4+T5+T6<f/1.02;
1.71<nL1, nL2, nL5, nL6<1.79; and
1.67<nL3, nL4<1.81

Where: r1 represents a radius of curvature of the collimated side surface of a first lens element; r2 represents a radius of curvature of an image side surface of a first lens element; r3 represents a radius of curvature of an collimated side surface of a second lens element; r4 represents a radius of curvature of an image side surface of the second lens element; r8 represents a radius of curvature of an object side surface of a fifth lens element; r9 represents a radius of curvature of an image side surface of the fifth lens element; T1 represents a thickness of the first lens element; T2 represents a thickness of the second lens element; T3 represents a thickness of the third lens element; T4 represents a thickness of the fourth lens element; T5 represents a thickness of the fifth lens element; nL1 represents an index of refraction of the first lens element; nL2 represents an index of refraction of the second lens element; n3 represents an index of refraction of the third lens element; nL4 represents an index of refraction of the fourth lens element; nL5 represents an index of refraction of the fifth lens element.

Figure 2:
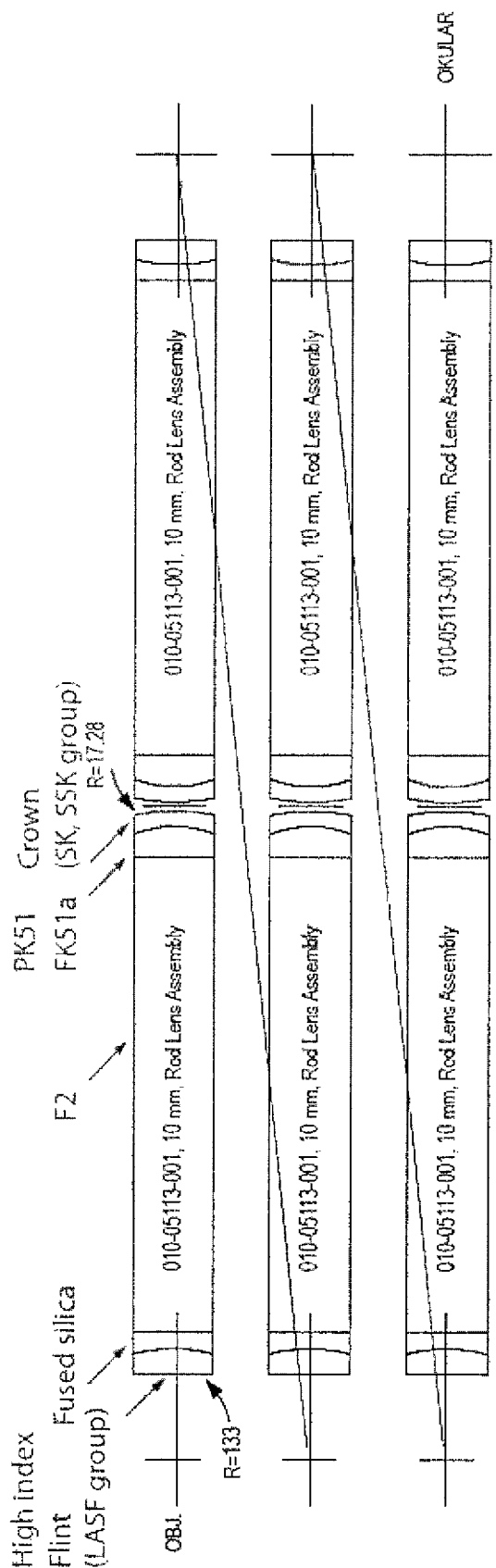
FIG. 2 is an engineering drawing of an embodiment of the rod lens assembly of the present invention.
Figure 3:
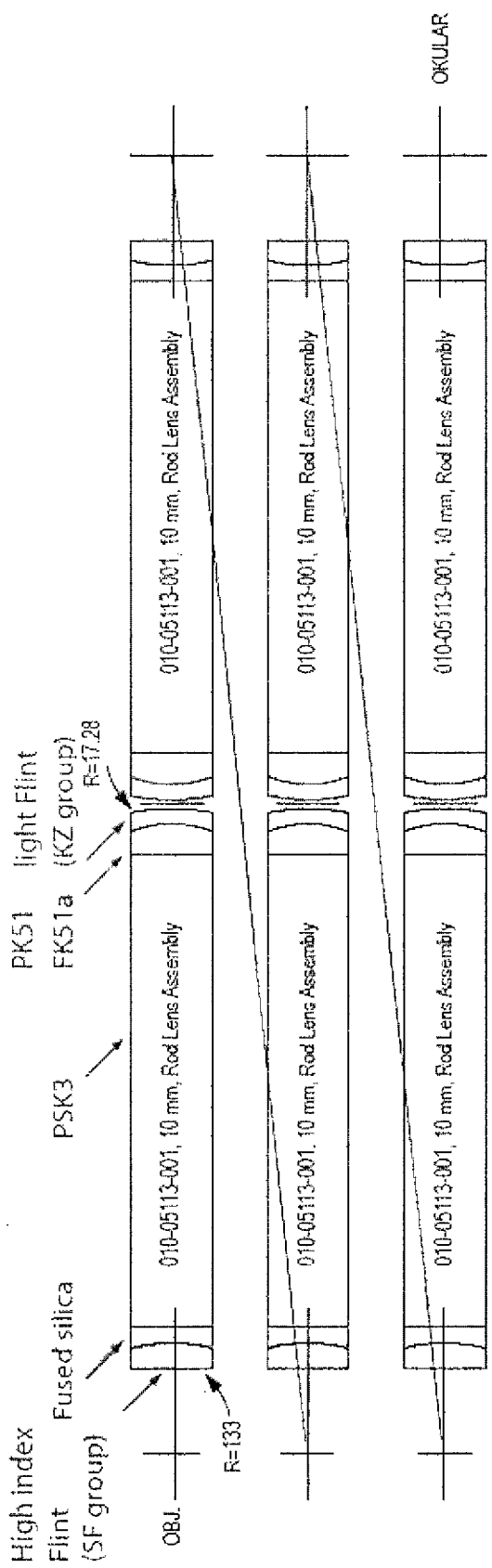
FIG. 3 is an engineering drawing of an alternate embodiment of the rod lens assembly of the present invention.

The various embodiments of the present invention provide image correction over a wide waveband range to allow co-located visible and near infrared images to be resolved on a single detector or, in the alternative, on multiplexed detector systems. Embodiments satisfying these criteria will result in a depth of focus over the desired waveband range. FIGS. 2 and 3 are representative embodiments that satisfy the above criteria. Those of skill in the art will understand that the glass choices shown in FIGS. 2 and 3 could easily be substituted with glass choices exhibiting similar properties or with glass choices of other manufacturers as long as the above criteria are satisfied.

The following tables provide data on working examples of embodiments of rod lens assemblies according to the present invention.

| SURFACE DATA SUMMARY: B1 | | | | | | |
|---|---|---|---|---|---|---|
| Surf Comment | Type | Radius | Thickness | Glass | Diameter | Conic |
| OBJ | STANDARD | Infinity | 6.383754 | | 4.2 | 0 |
| 1 | STANDARD | 84.65 | 2.25 | N-LASF41 | 6.48 | 0 |
| 2 | STANDARD | −16.53 | 1.5 | LITHOSIL-Q | 6.48 | 0 |
| 3 | STANDARD | Infinity | 43 | F2 | 6.48 | 0 |
| 4 | STANDARD | Infinity | 2.5 | N-PK51 | 6.48 | 0 |
| 5 | STANDARD | −10.38 | 1.2 | N-LASF44 | 6.48 | 0 |
| 6 | STANDARD | −15.95 | 0.4 | | 6.48 | 0 |
| STO | STANDARD | Infinity | 0.4 | | 5.227259 | 0 |
| 8 | STANDARD | 15.95 | 1.2 | N-LASF44 | 6.48 | 0 |
| 9 | STANDARD | 10.38 | 2.5 | N-PK51 | 6.48 | 0 |
| 10 | STANDARD | Infinity | 43 | F2 | 6.48 | 0 |
| 11 | STANDARD | Infinity | 1.5 | LITHOSIL-Q | 6.48 | 0 |
| 12 | STANDARD | 16.53 | 2.25 | N-LASF41 | 6.48 | 0 |
| 13 | STANDARD | −84.65 | 6.383755 | | 6.48 | 0 |
| IMA | STANDARD | −14.46627 | | | 4.202416 | 0 |

| SURFACE DATA SUMMARY: B9 | | | | | | |
|---|---|---|---|---|---|---|
| Surf Comment | Type | Radius | Thickness | Glass | Diameter | Conic |
| OBJ | STANDARD | Infinity | 6.529348 | | 4.2 | 0 |
| 1 | STANDARD | 77.03 | 2.25 | N-LASF45 | 6.48 | 0 |
| 2 | STANDARD | −14.739 | 1.2 | LITHOSIL-Q | 6.48 | 0 |
| 3 | STANDARD | Infinity | 41.9 | F2 | 6.48 | 0 |
| 4 | STANDARD | Infinity | 2.245 | N-PK51 | 6.48 | 0 |
| 5 | STANDARD | −10.24 | 1.4 | N-LASF41 | 6.48 | 0 |
| 6 | STANDARD | −15.55 | 0.4 | | 6.48 | 0 |
| STO | STANDARD | Infinity | 0.4 | | 5.124602 | 0 |
| 8 | STANDARD | 15.55 | 1.4 | N-LASF41 | 6.48 | 0 |
| 9 | STANDARD | 10.24 | 2.245 | N-PK51 | 6.48 | 0 |
| 10 | STANDARD | Infinity | 41.9 | F2 | 6.48 | 0 |
| 11 | STANDARD | Infinity | 1.2 | LITHOSIL-Q | 6.48 | 0 |
| 12 | STANDARD | 14.739 | 2.25 | N-LASF45 | 6.48 | 0 |
| 13 | STANDARD | −77.03 | 6.529348 | | 6.48 | 0 |
| IMA | STANDARD | −14.1181 | | | 4.202722 | 0 |

| SURFACE DATA SUMMARY: B8 | | | | | | |
|---|---|---|---|---|---|---|
| Surf Comment | Type | Radius | Thickness | Glass | Diameter | Conic |
| OBJ | STANDARD | Infinity | 6.811963 | | 4.2 | 0 |
| 1 | STANDARD | 74.98 | 2.25 | N-LASF40 | 6.48 | 0 |
| 2 | STANDARD | −16.4 | 1.49 | LITHOSIL-Q | 6.48 | 0 |
| 3 | STANDARD | Infinity | 41 | F2 | 6.48 | 0 |
| 4 | STANDARD | Infinity | 2.254 | N-FK51A | 6.48 | 0 |
| 5 | STANDARD | −9.5 | 1.4 | N-LAF21 | 6.48 | 0 |
| 6 | STANDARD | −14.28 | 0.4 | | 6.48 | 0 |
| STO | STANDARD | Infinity | 0.4 | | 5.073546 | 0 |
| 8 | STANDARD | 14.28 | 1.4 | N-LAF21 | 6.48 | 0 |
| 9 | STANDARD | 9.5 | 2.254 | N-FK51A | 6.48 | 0 |
| 10 | STANDARD | Infinity | 41 | F2 | 6.48 | 0 |
| 11 | STANDARD | Infinity | 1.49 | LITHOSIL-Q | 6.48 | 0 |
| 12 | STANDARD | 16.4 | 2.25 | N-LASF40 | 6.48 | 0 |
| 13 | STANDARD | −74.98 | 6.811963 | | 6.48 | 0 |
| IMA | STANDARD | −14.03906 | | | 4.201983 | 0 |

| SURFACE DATA SUMMARY: B7 | | | | | | |
|---|---|---|---|---|---|---|
| Surf Comment | Type | Radius | Thickness | Glass | Diameter | Conic |
| OBJ | STANDARD | Infinity | 7.179675 | | 4.2 | 0 |
| 1 | STANDARD | 77.7 | 2.25 | N-LASF41 | 6.48 | 0 |
| 2 | STANDARD | −16 | 1.23 | LITHOSIL-Q | 6.48 | 0 |
| 3 | STANDARD | Infinity | 41 | F2 | 6.48 | 0 |
| 4 | STANDARD | Infinity | 2.254 | N-FK51A | 6.48 | 0 |
| 5 | STANDARD | −9.64 | 1.4 | N-LAF21 | 6.48 | 0 |
| 6 | STANDARD | −14.478 | 0.4 | | 6.48 | 0 |
| STO | STANDARD | Infinity | 0.4 | | 5.016918 | 0 |
| 8 | STANDARD | 14.478 | 1.4 | N-LAF21 | 6.48 | 0 |
| 9 | STANDARD | 9.64 | 2.254 | N-FK51A | 6.48 | 0 |
| 10 | STANDARD | Infinity | 41 | F2 | 6.48 | 0 |
| 11 | STANDARD | Infinity | 1.23 | LITHOSIL-Q | 6.48 | 0 |
| 12 | STANDARD | 16 | 2.25 | N-LASF41 | 6.48 | 0 |
| 13 | STANDARD | −77.7 | 7.179675 | | 6.48 | 0 |
| IMA | STANDARD | −14.19567 | | | 4.202639 | 0 |

| SURFACE DATA SUMMARY: B6 | | | | | | |
|---|---|---|---|---|---|---|
| Surf Comment | Type | Radius | Thickness | Glass | Diameter | Conic |
| OBJ | STANDARD | Infinity | 6.5 | | 4.2 | 0 |
| 1 | STANDARD | 86.17 | 2.214402 | N-LASF41 | 6.48 | 0 |
| 2 | STANDARD | −16.36 | 1.499883 | LITHOSIL-Q | 6.48 | 0 |
| 3 | STANDARD | Infinity | 42.9999 | F2 | 6.48 | 0 |
| 4 | STANDARD | Infinity | 2.499888 | N-PK51 | 6.48 | 0 |
| 5 | STANDARD | −10.40045 | 1.100332 | N-LASF44 | 6.48 | 0 |
| 6 | STANDARD | −15.95579 | 0.4 | | 6.48 | 0 |
| STO | STANDARD | Infinity | 0.4 | | 5.208597 | 0 |
| 8 | STANDARD | 15.95579 | 1.100332 | N-LASF44 | 6.48 | 0 |
| 9 | STANDARD | 10.40045 | 2.499888 | N-PK51 | 6.48 | 0 |
| 10 | STANDARD | Infinity | 42.9999 | F2 | 6.48 | 0 |
| 11 | STANDARD | Infinity | 1.499883 | LITHOSIL-Q | 6.48 | 0 |
| 12 | STANDARD | 16.36 | 2.214402 | N-LASF41 | 6.48 | 0 |
| 13 | STANDARD | −86.17 | 6.5 | | 6.48 | 0 |
| IMA | STANDARD | −14.45692 | | | 4.202283 | 0 |

| SURFACE DATA SUMMARY: B5 | | | | | | |
|---|---|---|---|---|---|---|
| Surf Comment | Type | Radius | Thickness | Glass | Diameter | Conic |
| OBJ | STANDARD | Infinity | 7.200016 | | 4.2 | 0 |
| 1 | STANDARD | 103.52 | 2.250002 | N-LASF31A | 6.48 | 0 |
| 2 | STANDARD | −17.7 | 1.500087 | LITHOSIL-Q | 6.48 | 0 |

-continued

SURFACE DATA SUMMARY: B5

| Surf Comment | Type | Radius | Thickness | Glass | Diameter | Conic |
|---|---|---|---|---|---|---|
| 3 | STANDARD | Infinity | 43 | F2 | 6.48 | 0 |
| 4 | STANDARD | Infinity | 2.5 | N-PK51 | 6.48 | 0 |
| 5 | STANDARD | −9.39 | 1.400003 | N-SSK8 | 6.48 | 0 |
| 6 | STANDARD | −18.59 | 0.4 | | 6.48 | 0 |
| STO | STANDARD | Infinity | 0.4 | | 5.207273 | 0 |
| 8 | STANDARD | 18.59 | 1.400003 | N-SSK8 | 6.48 | 0 |
| 9 | STANDARD | 9.39 | 2.5 | N-PK51 | 6.48 | 0 |
| 10 | STANDARD | Infinity | 43 | F2 | 6.48 | 0 |
| 11 | STANDARD | Infinity | 1.500087 | LITHOSIL-Q | 6.48 | 0 |
| 12 | STANDARD | 17.7 | 2.250002 | N-LASF31A | 6.48 | 0 |
| 13 | STANDARD | −103.52 | 7.200016 | | 6.48 | 0 |
| IMA | STANDARD | −15.74497 | | | 4.20206 | 0 |

SURFACE DATA SUMMARY: B4 psk3

| Surf Comment | Type | Radius | Thickness | Glass | Diameter | Conic |
|---|---|---|---|---|---|---|
| OBJ | STANDARD | Infinity | 8.009468 | | 4.2 | 0 |
| 1 | STANDARD | 84.4 | 2.16 | N-LASF40 | 6.48 | 0 |
| 2 | STANDARD | −17.57 | 1.5 | LITHOSIL-Q | 6.48 | 0 |
| 3 | STANDARD | Infinity | 43 | N-PSK3 | 6.48 | 0 |
| 4 | STANDARD | Infinity | 2.5 | N-PK51 | 6.48 | 0 |
| 5 | STANDARD | −9.645 | 1.4 | N-KZFS4 | 6.48 | 0 |
| 6 | STANDARD | −19.63 | 0.4 | | 6.48 | 0 |
| STO | STANDARD | Infinity | 0.4 | | 5.426728 | 0 |
| 8 | STANDARD | 19.63 | 1.4 | N-KZFS4 | 6.48 | 0 |
| 9 | STANDARD | 9.645 | 2.5 | N-PK51 | 6.48 | 0 |
| 10 | STANDARD | Infinity | 43 | N-PSK3 | 6.48 | 0 |
| 11 | STANDARD | Infinity | 1.5 | LITHOSIL-Q | 6.48 | 0 |
| 12 | STANDARD | 17.57 | 2.16 | N-LASF40 | 6.48 | 0 |
| 13 | STANDARD | −84.4 | 8.009468 | | 6.48 | 0 |
| IMA | STANDARD | −14.87987 | | | 4.20116 | 0 |

SURFACE DATA SUMMARY: B4

| Surf Comment | Type | Radius | Thickness | Glass | Diameter | Conic |
|---|---|---|---|---|---|---|
| OBJ | STANDARD | Infinity | 6.508687 | | 4.2 | 0 |
| 1 | STANDARD | 70.9 | 1.750006 | N-LAF21 | 6.48 | 0 |
| 2 | STANDARD | −15.45 | 1.5 | LITHOSIL-Q | 6.48 | 0 |
| 3 | STANDARD | Infinity | 43 | F2 | 6.48 | 0 |
| 4 | STANDARD | Infinity | 2.5 | N-FK51A | 6.48 | 0 |
| 5 | STANDARD | −9.58 | 1.398016 | N-LAK33A | 6.48 | 0 |
| 6 | STANDARD | −14.65972 | 0.4 | | 6.48 | 0 |
| STO | STANDARD | Infinity | 0.4 | | 5.262155 | 0 |
| 8 | STANDARD | 14.65972 | 1.398016 | N-LAK33A | 6.48 | 0 |
| 9 | STANDARD | 9.58 | 2.5 | N-FK51A | 6.48 | 0 |
| 10 | STANDARD | Infinity | 43 | F2 | 6.48 | 0 |
| 11 | STANDARD | Infinity | 1.5 | LITHOSIL-Q | 6.48 | 0 |
| 12 | STANDARD | 15.45 | 1.750006 | N-LAF21 | 6.48 | 0 |
| 13 | STANDARD | −70.9 | 6.508687 | | 6.48 | 0 |
| IMA | STANDARD | −13.96135 | | | 4.202042 | 0 |

SURFACE DATA SUMMARY: B3 psk3

| Surf Comment | Type | Radius | Thickness | Glass | Diameter | Conic |
|---|---|---|---|---|---|---|
| OBJ | STANDARD | Infinity | 8.01793 | | 4.2 | 0 |
| 1 | STANDARD | 109.1 | 1.85 | N-LASF41 | 6.48 | 0 |
| 2 | STANDARD | −15.95 | 1.5 | LITHOSIL-Q | 6.48 | 0 |
| 3 | STANDARD | Infinity | 43 | N-PSK3 | 6.48 | 0 |
| 4 | STANDARD | Infinity | 2.5 | N-PK51 | 6.48 | 0 |

-continued

SURFACE DATA SUMMARY: B3 psk3

| Surf Comment | Type | Radius | Thickness | Glass | Diameter | Conic |
|---|---|---|---|---|---|---|
| 5 | STANDARD | −9.81 | 1.4 | N-KZFS4 | 6.48 | 0 |
| 6 | STANDARD | −19.66 | 0.4 | | 6.48 | 0 |
| STO | STANDARD | Infinity | 0.4 | | 5.389994 | 0 |
| 8 | STANDARD | 19.66 | 1.4 | N-KZFS4 | 6.48 | 0 |
| 9 | STANDARD | 9.81 | 2.5 | N-PK51 | 6.48 | 0 |
| 10 | STANDARD | Infinity | 43 | N-PSK3 | 6.48 | 0 |
| 11 | STANDARD | Infinity | 1.5 | LITHOSIL-Q | 6.48 | 0 |
| 12 | STANDARD | 15.95 | 1.85 | N-LASF41 | 6.48 | 0 |
| 13 | STANDARD | −109.1 | 8.01793 | | 6.48 | 0 |
| IMA | STANDARD | −15.73277 | | | 4.201634 | 0 |

SURFACE DATA SUMMARY: B3

| Surf Comment | Type | Radius | Thickness | Glass | Diameter | Conic |
|---|---|---|---|---|---|---|
| OBJ | STANDARD | Infinity | 8.270844 | | 4.2 | 0 |
| 1 | STANDARD | 107 | 2.25 | N-LASF31A | 6.48 | 0 |
| 2 | STANDARD | −16.87 | 1.499996 | LITHOSIL-Q | 6.48 | 0 |
| 3 | STANDARD | Infinity | 41.43 | F2 | 6.48 | 0 |
| 4 | STANDARD | Infinity | 2.500002 | N-FK51A | 6.48 | 0 |
| 5 | STANDARD | −8.459549 | 1.4 | N-BALF5 | 6.48 | 0 |
| 6 | STANDARD | −18.08 | 0.4 | | 6.48 | 0 |
| STO | STANDARD | Infinity | 0.4 | | 5.058103 | 0 |
| 8 | STANDARD | 18.08 | 1.4 | N-BALF5 | 6.48 | 0 |
| 9 | STANDARD | 8.459549 | 2.500002 | N-FK51A | 6.48 | 0 |
| 10 | STANDARD | Infinity | 41.43 | F2 | 6.48 | 0 |
| 11 | STANDARD | Infinity | 1.499996 | LITHOSIL-Q | 6.48 | 0 |
| 12 | STANDARD | 16.87 | 2.25 | N-LASF31A | 6.48 | 0 |
| 13 | STANDARD | −107 | 8.270844 | | 6.48 | 0 |
| IMA | STANDARD | −15.4475 | | | 4.201743 | 0 |

SURFACE DATA SUMMARY: B2 psk3

| Surf Comment | Type | Radius | Thickness | Glass | Diameter | Conic |
|---|---|---|---|---|---|---|
| OBJ | STANDARD | Infinity | 8.026638 | | 4.2 | 0 |
| 1 | STANDARD | 94.1 | 2.25 | N-LAF21 | 6.48 | 0 |
| 2 | STANDARD | −14.4 | 1.5 | LITHOSIL-Q | 6.48 | 0 |
| 3 | STANDARD | Infinity | 42.98 | N-PSK3 | 6.48 | 0 |
| 4 | STANDARD | Infinity | 2.5 | N-PK51 | 6.48 | 0 |
| 5 | STANDARD | −9.98 | 1.4 | N-KZFS4 | 6.48 | 0 |
| 6 | STANDARD | −19.88 | 0.4 | | 6.48 | 0 |
| STO | STANDARD | Infinity | 0.4 | | 5.384559 | 0 |
| 8 | STANDARD | 19.88 | 1.4 | N-KZFS4 | 6.48 | 0 |
| 9 | STANDARD | 9.98 | 2.5 | N-PK51 | 6.48 | 0 |
| 10 | STANDARD | Infinity | 42.98 | N-PSK3 | 6.48 | 0 |
| 11 | STANDARD | Infinity | 1.5 | LITHOSIL-Q | 6.48 | 0 |
| 12 | STANDARD | 14.4 | 2.25 | N-LAF21 | 6.48 | 0 |
| 13 | STANDARD | −94.1 | 8.026639 | | 6.48 | 0 |
| IMA | STANDARD | −14.73027 | | | 4.20289 | 0 |

SURFACE DATA SUMMARY: B2

| Surf Comment | Type | Radius | Thickness | Glass | Diameter | Conic |
|---|---|---|---|---|---|---|
| OBJ | STANDARD | Infinity | 6.933147 | | 4.2 | 0 |
| 1 | STANDARD | 85.7 | 1.749944 | N-LASF44 | 6.48 | 0 |
| 2 | STANDARD | −15 | 1.481913 | LITHOSIL-Q | 6.48 | 0 |
| 3 | STANDARD | Infinity | 43 | F2 | 6.48 | 0 |
| 4 | STANDARD | Infinity | 2.5 | N-PK51 | 6.48 | 0 |
| 5 | STANDARD | −7.97 | 1.399903 | N-BAK4 | 6.48 | 0 |
| 6 | STANDARD | −19.27 | 0.358 | | 6.48 | 0 |

-continued

SURFACE DATA SUMMARY: B2

| Surf Comment | Type | Radius | Thickness | Glass | Diameter | Conic |
|---|---|---|---|---|---|---|
| STO | STANDARD | Infinity | 0.358 | | 5.175835 | 0 |
| 8 | STANDARD | 19.27 | 1.399903 | N-BAK4 | 6.48 | 0 |
| 9 | STANDARD | 7.97 | 2.5 | N-PK51 | 6.48 | 0 |
| 10 | STANDARD | Infinity | 43 | F2 | 6.48 | 0 |
| 11 | STANDARD | Infinity | 1.481913 | LITHOSIL-Q | 6.48 | 0 |
| 12 | STANDARD | 15 | 1.749944 | N-LASF44 | 6.48 | 0 |
| 13 | STANDARD | −85.7 | 6.933147 | | 6.48 | 0 |
| IMA | STANDARD | −14.75403 | | | 4.20195 | 0 |

SURFACE DATA SUMMARY: B1 psk3

| Surf Comment | Type | Radius | Thickness | Glass | Diameter | Conic |
|---|---|---|---|---|---|---|
| OBJ | STANDARD | Infinity | 9.303554 | | 4.2 | 0 |
| 1 | STANDARD | 139.8 | 2.25 | N-LASF31A | 6.48 | 0 |
| 2 | STANDARD | −16.95 | 1.5 | LITHOSIL-Q | 6.48 | 0 |
| 3 | STANDARD | Infinity | 42.98 | PSK3 | 6.48 | 0 |
| 4 | STANDARD | Infinity | 2.5 | N-PK51 | 6.48 | 0 |
| 5 | STANDARD | −10.96 | 1.4 | N-KZFS5 | 6.48 | 0 |
| 6 | STANDARD | −20.17 | 0.358 | | 6.48 | 0 |
| STO | STANDARD | Infinity | 0.358 | | 5.405834 | 0 |
| 8 | STANDARD | 20.17 | 1.4 | N-KZFS5 | 6.48 | 0 |
| 9 | STANDARD | 10.96 | 2.5 | N-PK51 | 6.48 | 0 |
| 10 | STANDARD | Infinity | 42.98 | PSK3 | 6.48 | 0 |
| 11 | STANDARD | Infinity | 1.5 | LITHOSIL-Q | 6.48 | 0 |
| 12 | STANDARD | 16.95 | 2.25 | N-LASF31A | 6.48 | 0 |
| 13 | STANDARD | −139.8 | 9.303554 | | 6.48 | 0 |
| IMA | STANDARD | −16.51157 | | | 4.202587 | 0 |

SURFACE DATA SUMMARY: B0 psk3

| Surf Comment | Type | Radius | Thickness | Glass | Diameter | Conic |
|---|---|---|---|---|---|---|
| OBJ | STANDARD | Infinity | 6.8 | | 4.2 | 0 |
| 1 | STANDARD | 99 | 2 | N-LASF41 | 6.48 | 0 |
| 2 | STANDARD | −16.16 | 1.295 | LITHOSIL-Q | 6.48 | 0 |
| 3 | STANDARD | Infinity | 42.75 | N-PSK3 | 6.48 | 0 |
| 4 | STANDARD | Infinity | 2.495 | N-PK51 | 6.48 | 0 |
| 5 | STANDARD | −9.744732 | 1.2 | N-KZFS4 | 6.48 | 0 |
| 6 | STANDARD | −18.77953 | 0.358 | | 6.48 | 0 |
| STO | STANDARD | Infinity | 0.358 | | 5.281348 | 0 |
| 8 | STANDARD | 18.77953 | 1.2 | N-KZFS4 | 6.48 | 0 |
| 9 | STANDARD | 9.744732 | 2.495 | N-PK51 | 6.48 | 0 |
| 10 | STANDARD | Infinity | 42.75 | N-PSK3 | 6.48 | 0 |
| 11 | STANDARD | Infinity | 1.295 | LITHOSIL-Q | 6.48 | 0 |
| 12 | STANDARD | 16.16 | 2 | N-LASF41 | 6.48 | 0 |
| 13 | STANDARD | −99 | 6.8 | | 6.48 | 0 |
| IMA | STANDARD | −14.26171 | | | 4.203002 | 0 |

What is claimed is:

1. A highly corrected relay system for an endoscope, comprising:
 a plurality of bonded lenses, wherein the plurality of bonded lenses is selected to provide color correction from the blue region of the spectrum through to the near infrared region of the spectrum, wherein light from the blue region of the spectrum through to the near infrared region of the spectrum follows a same optical path, and wherein the system allows co-located visible and near infrared images to be resolved on a single detector; and
 a symmetrical pair of rod lens assemblies, wherein each rod lens assembly includes
  a first bi-convex lens;
  a second plano-concave lens;
  a third elongated plano/piano rod lens;
  a fourth plano-convex lens; and
  a fifth meniscus lens.

2. The highly corrected relay system of claim 1, wherein the color correction is provided from approximately 400 nm to approximately 900 nm.

3. The highly corrected relay system of claim 1, wherein the pair of rod lens assemblies is arranged around an air space containing a centered pupil and aperture stop position.

4. A highly corrected relay system for an endoscope providing color correction from the blue region of the spectrum through to the near infrared region of the spectrum, and wherein the system allows co-located visible and near infrared images to be resolved on a single detector, comprising a symmetrical pair of rod lens assemblies including a plurality of lens elements and an aperture location, each element having a lens surface defined by a radius of curvature (r), a thickness (t), an index of refraction (n), and a dispersion value (v), the plurality of lens elements being spaced from each other, an object to be viewed and an image of the object by a distance (h) and wherein the assembly satisfies two or more of the following conditions:

$1000 < r4/r2$ or $r4=r2=$approximately infinity;
$-0.56 < r3/r9 < -0.81$;
$0.9 < r8/r9 < 1.1$ or $r8=r9$;
$0.9 < r10/r11 < 1.1$ or $r10=r11$;
$0.7 < (h1+h2)/(h3+h4) < 1.1$;
$0.95 < h1+h2+h3+h4+T1+T2+T3+T4+T5+T6 < f/1.02$;
$1.71 < nL1, nL2, nL5, nL6 < 1.79$; and
$1.67 < nL3, nL4 < 1.81$ Where: r1 represents a radius of curvature of the collimated side surface of a first lens element; r2 represents a radius of curvature of an image side surface of a first lens element; r3 represents a radius of curvature of an collimated side surface of a second lens element; r4 represents a radius of curvature of an image side surface of the second lens element; r8 represents a radius of curvature of an object side surface of a fifth lens element; r9 represents a radius of curvature of an object side surface of the fifth lens element; T1 represents a thickness of the first lens element; T2 represents a thickness of the second lens element; T3 represents a thickness of the third lens element; T4 represents a thickness of the fourth lens element; T5 represents a thickness of the fifth lens element; nL1 represents an index of refraction of the first lens element; nL2 represents an index of refraction of the second lens element; n3 represents an index of refraction of the third lens element; nL4 represents an index of refraction of the fourth lens element; nL5 represents an index of refraction of the fifth lens element.

5. The highly correlated relay system of claim 4, wherein the assembly satisfies three or more of the conditions.

6. The highly correlated relay system of claim 4, wherein light from the blue region of the spectrum through to the near infrared region of the spectrum follows a same optical path.

* * * * *